(12) United States Patent
Nadkarni et al.

(10) Patent No.: US 9,629,818 B2
(45) Date of Patent: Apr. 25, 2017

(54) PHARMACEUTICAL COMPOSITION OF TAPENTADOL FOR PARENTERAL ADMINISTRATION

(71) Applicant: TORRENT PHARMACEUTICALS LTD, Ahmedabad (IN)

(72) Inventors: Sunil Sadanand Nadkarni, Gandhinagar (IN); Jaya Abraham, Gandhinagar (IN); Kapil Khatri, Gandhinagar (IN)

(73) Assignee: TORRENT PHARMACEUTICALS LTD., Gujarat (IN)

( * ) Notice: Subject to any disclaimer, the term of this patent is extended or adjusted under 35 U.S.C. 154(b) by 0 days.

(21) Appl. No.: 14/439,840

(22) PCT Filed: Nov. 1, 2012

(86) PCT No.: PCT/IB2012/056082
§ 371 (c)(1),
(2) Date: Apr. 30, 2015

(87) PCT Pub. No.: WO2014/068372
PCT Pub. Date: May 8, 2014

(65) Prior Publication Data
US 2015/0290146 A1    Oct. 15, 2015

(51) Int. Cl.
| | | |
|---|---|---|
| *A61K 31/137* | (2006.01) |
| *A61K 9/19* | (2006.01) |
| *A61K 9/10* | (2006.01) |
| *A61K 9/127* | (2006.01) |
| *A61K 9/00* | (2006.01) |
| *A61K 9/14* | (2006.01) |
| *A61K 47/14* | (2017.01) |
| *A61K 47/26* | (2006.01) |
| *A61K 47/32* | (2006.01) |
| *A61K 47/38* | (2006.01) |
| *A61K 47/44* | (2017.01) |
| *A61K 9/16* | (2006.01) |
| *A61K 47/22* | (2006.01) |
| *A61K 47/34* | (2017.01) |

(52) U.S. Cl.
CPC .......... *A61K 31/137* (2013.01); *A61K 9/0019* (2013.01); *A61K 9/0024* (2013.01); *A61K 9/10* (2013.01); *A61K 9/127* (2013.01); *A61K 9/14* (2013.01); *A61K 9/1647* (2013.01); *A61K 9/19* (2013.01); *A61K 47/14* (2013.01); *A61K 47/22* (2013.01); *A61K 47/26* (2013.01); *A61K 47/32* (2013.01); *A61K 47/34* (2013.01); *A61K 47/38* (2013.01); *A61K 47/44* (2013.01)

(58) Field of Classification Search
None
See application file for complete search history.

(56) References Cited

U.S. PATENT DOCUMENTS

| | | | |
|---|---|---|---|
| 2011/0071120 A1* | 3/2011 | Khunt | C07C 59/245 514/166 |
| 2012/0022117 A1 | 1/2012 | Gruss et al. | |
| 2012/0225951 A1 | 9/2012 | Christoph et al. | |
| 2012/0237561 A1* | 9/2012 | Faassen | A61K 9/0019 424/400 |

FOREIGN PATENT DOCUMENTS

| | | | |
|---|---|---|---|
| WO | WO 2011/107876 A2 * | 9/2011 | |
| WO | 2011/139595 A2 | 11/2011 | |

* cited by examiner

*Primary Examiner* — Jeffrey Washville
(74) *Attorney, Agent, or Firm* — Volpe and Koenig, P.C.

(57) ABSTRACT

The present invention relates to a pharmaceutical composition of tapentadol for parenteral administration which provides prolonged release of tapentadol. Present invention also relates to the process of preparation of pharmaceutical composition of tapentadol for parenteral administration and its use in the treatment of pain.

16 Claims, 2 Drawing Sheets

PHARMACEUTICAL COMPOSITION OF TAPENTADOL FOR PARENTERAL ADMINISTRATION

CROSS REFERENCE TO RELATED APPLICATIONS

Figure 1:
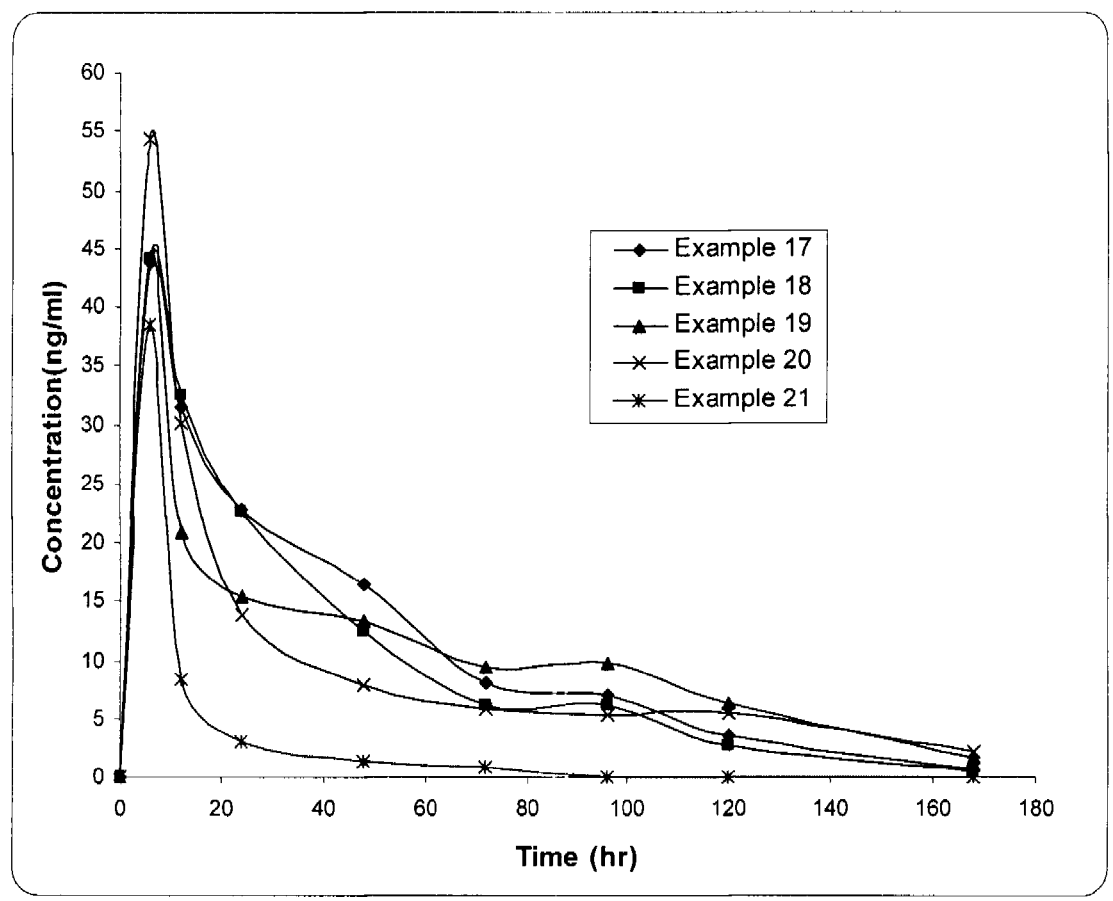

This application is a 35 U.S.C. §371 national stage application of PCT/IB2012/058082, which was filed Nov. 1, 2012 and is incorporated herein by reference as if fully set forth.

FIELD OF THE INVENTION

The present invention relates to injectable compositions of tapentadol or its pharmaceutically acceptable salt or ester for prolonged delivery, their preparation and use in treatment of pain.

BACKGROUND OF THE INVENTION

Pain is an unpleasant sensory and emotional experience associated with actual or potential tissue damage, or described in terms of such damages. Pain may be classified by etiology, duration and severity. Etiologically, pain may be classified as somatogenic (i.e. organic) or psychogenic (occurring without associated organic pathology sufficient to explain the severity and/or duration of the pain). Somatogenic pain may be further sub-classified as nociceptive (arising out of stimulation of somatic or visceral pain-sensitive nerve fibers) or neuropathic (resulting from dysfunction of the nervous system). With regard to duration, pain is generally categorized as either acute or chronic. Chronic persistent pain can cause significant impairment of physical and psychological health, and performance of social responsibilities, including work and family life. Chronic pain has been described as pain that has persisted for at least 5 days to as long as 6 months. Chronic pain is generally associated with conditions like surgery, cancer, severe injury etc. Opioids are generally used to control the severe chronic pain conditions. Although opioids are powerful analgesics, benefits are somewhat limited by relatively short half life. Since pain from the procedures described can last several days, these analgesics must be administered many times in order to be effective in controlling pain.

Tapentadol is opioid analgesic having both μ-opioid receptor agonist and noradrenalin (Norepinephrine) reuptake inhibition activity with minimal serotonin reuptake inhibition. This dual mode of action makes tapentadol particularly useful in the treatment of both nociceptive pain and neuropathic pain. Clinical trial evidence in acute and chronic non-cancer pain and neuropathic pain supports an opioid-sparing effect that reduces some of the typical opioid-related adverse effects. Specifically, the reduction in treatment-emergent gastrointestinal adverse effects for tapentadol compared with equianalgesic pure μ-opioid receptor agonist results in improved tolerability and adherence to therapy.

U.S. Pat. No. 6,248,737 discloses tapentadol and its hydrochloride salt. Tapentadol is available commercially as a brand name NUCYNTA® as an immediate release oral tablet, indicated for the relief of moderate to severe acute pain and PALEXIA® RETARD as prolonged release tablet, indicated for severe chronic pain.

When tapentadol is given orally, it undergoes extensive first pass metabolism, which leads to low bioavailability (32%). About 97% of the parent compound is metabolized. None of the metabolites contributes to the analgesic activity. Eventually, the desired action is only achieved with high dose of tapentadol. Immediate release oral tapentadol is administered every 4-6 hrs while sustained release tablet is administered every 12 hrs interval. Being an opioid analgesic, tapentadol is used for the treatment of severe pain such as post operative pain, cancer pain etc. In such cases nausea & vomiting is a frequently associated problem and hence poor patient compliance is seen with oral administration. Some drawbacks to the oral administration are that unit dose may be improperly modified by a patient, resulting in a dangerous overdose, or the patient may not be capable of swallowing the medication.

Tapentadol has short duration of action which compel patient to take frequent administration of tapentadol. Additionally, like other opioids, tapentadol is also known to have abuse potential. To combat this problem, U.S. Pat. No. 8,075,872 provides abuse proof controlled release formulation of tapentadol for oral administration, for twice a daily administration.

Thus, there exists a need for an alternative dosage form, which provides prolonged release of tapentadol thereby reduces the frequency of administration. Further the alternative dosage form is required to overcome the problem associated with oral administration and to reduce the chances of abuse so that the release of the analgesic can not be manipulated by the patient or other external sources.

Tapentadol has relatively less potential to tolerance as compared to other opioids which make this the drug of choice, to be formulated for prolonged delivery among the other opioids.

Inventors of present invention have developed a new dosage form for parenteral administration, which provide prolonged release of tapentadol. Since the analgesic effect of tapentadol remains for short duration (maximum 12 hours), prolongation of the action of the drugs would significantly benefit the patients by continuously maintaining a therapeutic level of pain relief. Prolonged release of tapentadol also overcomes the problem of inadequate relief of pain due to fluctuation in dosing frequency during oral therapy.

SUMMARY OF THE INVENTION

The first embodiment of the present invention provides an injectable composition comprising tapentadol or its pharmaceutically acceptable salt or ester wherein the said composition provides prolonged release of tapentadol.

Another embodiment of the present invention provides an injectable composition comprising tapentadol or its pharmaceutically acceptable salt or ester, wherein the said composition provides prolonged release of tapentadol for at least 24 hours.

Another embodiment of the present invention provides an injectable composition comprising tapentadol or its pharmaceutically acceptable salt or ester, wherein the said composition provides prolonged release of tapentadol up to 1 month, preferably up to 15 days, more preferably up to 7 days, most preferably up to 5 days.

Another embodiment of the present invention provides an injectable composition comprising tapentadol or its pharmaceutically acceptable salt or ester, formulated as solid implant, in-situ implant, microparticle, in-situ microparticle, liposomal or liquid composition and wherein the said composition provides prolonged release of tapentadol.

Another embodiment of the present invention provides an injectable composition comprising tapentadol monopamoate or hemipamoate, and wherein the said composition provides prolonged release of tapentadol.

Another embodiment of the present invention provides an injectable composition comprising tapentadol monopamoate or hemipamoate formulated as liquid composition wherein the said composition provides prolonged release of tapentadol.

Another embodiment of the present invention provides an injectable composition comprising engineered particles of tapentadol or its pharmaceutically acceptable salt or ester formulated as liquid composition, wherein the said composition provides prolonged release of tapentadol.

Another embodiment of the present invention provides an injectable composition comprising engineered particles of tapentadol or its pharmaceutically acceptable salt or ester formulated as aqueous or non-aqueous suspension, wherein the said composition provides prolonged release of tapentadol.

Another embodiment of the present invention provides an injectable composition comprising engineered particles of tapentadol hemipamoate in the form of liquid composition wherein the said composition provides prolonged release of tapentadol for up to 15 days, preferably for up to 7 days, most preferably for up to 5 days.

Another embodiment of the present invention provides process for preparing an injectable composition comprising tapentadol or its pharmaceutically acceptable salt or ester, and wherein the said composition provides prolonged release of tapentadol.

FIG. 1: Comparative pK profiles of tapentadol hemipamoate aqueous suspensions and tapentadol microparticles in Wistar Rats.

Figure 2:
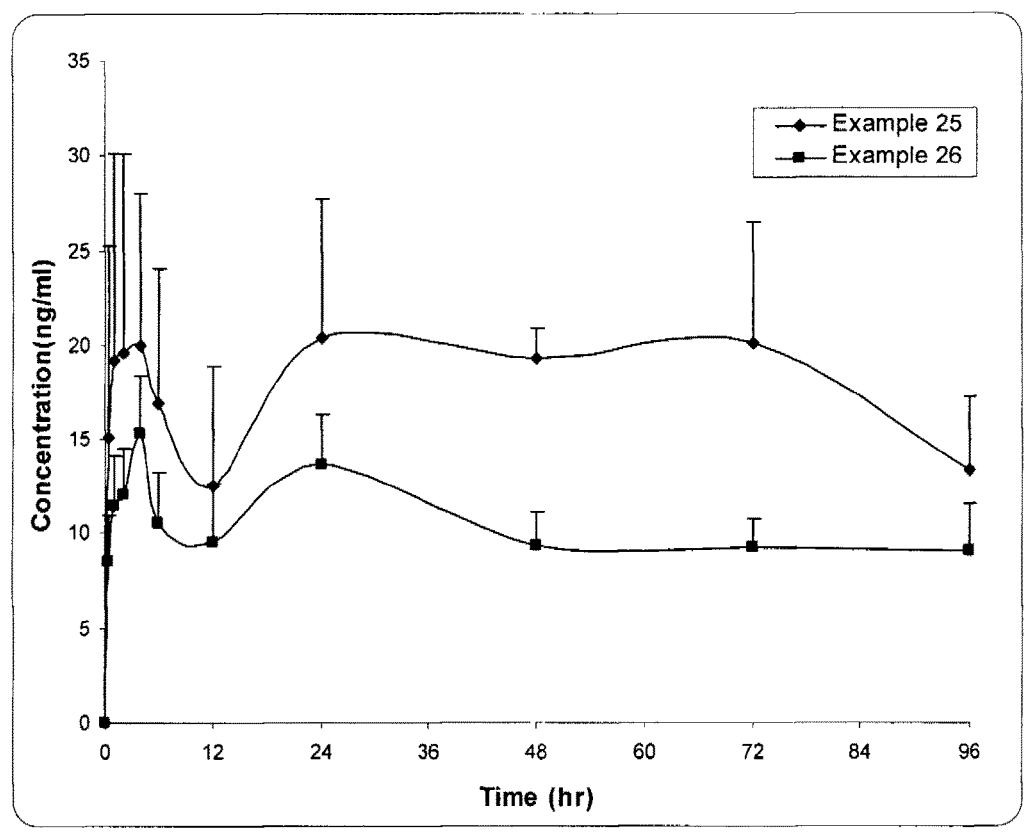

FIG. 2: Comparative pK profiles of tapentadol hemipamoate reconstituted lyophilized powder in Beagle Dogs

DETAILED DESCRIPTION OF THE INVENTION

The term "Tapentadol" as used herein refers to (−)-(1R, 2R)-3-(3-dimethylamino-1-ethyl-2-methyl-propyl)-phenol.

The term "active agent" or "drug" as used herein is defined to mean at least one form of tapentadol chosen from tapentadol base, the individually optically active enantiomers of tapentadol, racemic mixtures thereof, active metabolites thereof, pharmaceutically acceptable soluble, sparingly soluble or insoluble salts and esters thereof or polymorph thereof, any of the said form can be crystalline or amorphous. Preferably tapentadol as a free base, insoluble or sparingly soluble salt or ester form of tapentadol is used for the present invention. The pharmaceutically acceptable salts of tapentadol according to the invention are acid addition salts wherein acid is selected from hydrochloric acid, hydrobromic acid, embonic acid, (2S,3S)-dibenzoyltartaric acid, dibenzoyltartaric acid, sebacic acid, 1-hydroxys-naphthoic acid, phosphoric acid, L-(+)-tartaric acid, lysinic acid, L-lysinic acid, D-(+)-malic acid, 4-methylbenzenesulfonic acid, ethanesulfonic acid, benzoic acid, cinnamic acid, L-(+)-lactic acid, S-(+)-mandelic acid, (+)-camphor-10-sulfonic acid, gluconic acid, L-(+)-ascorbic acid, ascorbic acid, palmitic acid, naphthalene-1,5-disulfonic acid, hexanoic acid, oleic acid, stearic acid, gentisic acid, octanoic acid, decanoic acid, nitric acid, orotic acid, mucic acid, alginic acid and acesulfamic acid, nicotinic acid, hydrogen bromide, sulfuric acid, acetic acid, propionic acid, oxalic acid, succinic acid, fumaric acid, maleic acid, cypionic acid, enanthic acid, fusidic acid, gluceptic acid, gluconic acid, lactobionic acid, lauric acid, valeric acid, terephthalic acid, hippuric acid, lactic acid, mandelic acid, malonic acid, malic acid, tartaric acid, methanesulfonic acid, citric acid, lactic acid. Preferably embonic acid/pamoic acid is used for preparation of salt of tapentadol. More preferably insoluble salts or sparingly soluble salts include monopamoate salt of tapentadol or hemipamoate salt of tapentadol. The esters of tapentadol according to present invention include but not limited to caprylate, caprate, laurate, myristate, palmitate, stearate, arachate, behenate, lignocerate, oleate, linoleate and the like, preferably ester is tapentadol palmitate. A skilled person can prepare esters and acid salts of tapentadol by following process known in the prior art for preparation of esters and salts of basic compounds.

The term "liquid composition or formulation" as used herein is defined as a solution, suspension or dispersion in aqueous or non-aqueous vehicle.

"In-situ implant" as used herein is used to indicate that gel or semisolid or solid implant structure is formed when a pharmaceutical composition is injected into a mammalian body and is intended to remain at the site of administration and releases the drug for a period of at least 24 hours, in the mammalian body, preferably for a period over 24 hours to one month.

"Solid implant" as used herein is used to indicate a solid composition, injected into a mammalian body and is intended to remain at the site of administration and release the drug for a period of at least 24 hours, in the mammalian body, preferably for a period over 24 hours to one month.

"Microparticles" or "Microspheres" as used herein means particles that comprise a polymer that serves as a matrix or binder of the particle. The microparticles contain an active agent dispersed or dissolved within the polymeric matrix. The polymer is preferably biodegradable and biocompatible.

In the present invention, the term "biodegradable" refers to a material that gradually decomposes, dissolves, hydrolyzes and/or erodes in vivo. Generally, the "biodegradable polymers" herein are polymers that are hydrolysable, and/or bioerodable in-situ primarily through hydrolysis and/or enzymolysis. The term "biodegradable polymer" as used herein is meant to include any biocompatible and/or biodegradable synthetic and natural polymers that can be used in vivo. Term "biocompatible" is meant not toxic to the body, is pharmaceutically acceptable, is not carcinogenic, and/or does not significantly induce inflammation in body tissues.

In accordance with the present invention, the meaning of the phrase "Prolonged release" is defined as release of active agent for at least 24 hours, preferably from 24 hours to one month, more preferably from 24 hours to 15 days, most preferably from 24 hours to 5 days.

"Coacervation" as used herein means a reversible, emulsoid stage existing between the sol and gel formations, in which the addition of a third substance causes the separation of the sol into two immiscible liquid phases, which can be called as phase separation.

"Supercritical fluid technology" as used herein means technology used for formation of small particles of a substance with a narrow size distribution by using supercritical fluids. This can be achieved by number of ways known in the prior art selected from rapidly exceeding the saturation point of a solute by dilution, depressurization and the like or a combination thereof. "Supercritical fluid" is any substance at a temperature and pressure above its critical point, examples of which includes but not limited to carbon dioxide, di-nitrogen oxide, carbon disulphide and the like.

Term "engineered particles" as used herein means the drug particles of tapentadol or its pharmaceutically acceptable salts, size and morphology of which is controlled for prolonged delivery of tapentadol or its pharmaceutically acceptable salts. Particles of the drug are subjected to a method or engineering techniques which controls the size of particles, methods or techniques include but not limited to air jet milling, ball milling, sonication, high pressure homogenizer, controlled precipitation, wet milling and the like. The desired size and morphology of the engineered particles is achieved based on the requirement of prolonged release of composition. The size (D90) may vary from 1 micron to 500 microns, so that engineered particles provide prolonged release of the active ingredient. Preferably size of engineered particles (D90) is less than 30 microns, more preferably size of engineered particles is less than 15 microns, most preferably size of engineered particles is less than 10 microns.

The use of the terms "a" and "an" and "the" and similar referents in the context of describing the invention are to be construed to cover both the singular and the plural, unless otherwise indicated herein or clearly contradicted by context.

Throughout this specification and the appended claims it is to be understood that the words "comprise" and "include" and variations such as "comprises", "comprising", "includes", "including" are to be interpreted inclusively, unless the context requires otherwise. That is, the use of these words may imply the inclusion of an element or elements not specifically recited.

The term "Mammal" as used herein means warm blooded animals, that can be human or non human (mice, rat, guinea pig, rabbit, dog), preferably human.

The first embodiment of the present invention is to provide an injectable composition comprises tapentadol or its pharmaceutically acceptable salt or ester, wherein the said composition provides prolonged release of tapentadol.

Another embodiment of the present invention provides an injectable composition comprises tapentadol or its pharmaceutically acceptable salt or ester, and wherein the said composition provides prolonged release of tapentadol for at least 24 hours.

Another embodiment of the present invention provides an injectable composition comprises tapentadol or its pharmaceutically acceptable salt or ester, and wherein the said composition provides prolonged release of tapentadol for up to one month, preferably up to 15 days, more preferable up to 7 days, most preferably up to 5 days.

Another embodiment of the present invention provides an injectable composition comprises engineered particles of tapentadol or its pharmaceutically acceptable salt or ester, wherein the said composition provides prolonged release of tapentadol.

Another embodiment of the present invention provides an injectable composition comprises engineered particles of tapentadol or its pharmaceutically acceptable salt or ester formulated as liquid composition, wherein the said composition provides prolonged release of tapentadol.

Another embodiment of the present invention provides an injectable composition comprises tapentadol or its pharmaceutically acceptable salt or ester, and wherein the particle size of tapentadol or its pharmaceutically acceptable salt or ester (D90) is less than 50 microns, preferably less than 30 microns, more preferably less than 15 microns, most preferably less than 10 microns and wherein the said composition provides prolonged release of tapentadol.

Another embodiment of the present invention provides an injectable composition comprising tapentadol or its pharmaceutically acceptable salt or ester, and wherein the pH of the composition is from 3-9, preferably 5-8.5.

Another embodiment of the present invention provides an injectable composition comprising tapentadol or its pharmaceutically acceptable salt or ester, formulated as a liquid composition, and wherein the said composition forms an in-situ implant upon contact with body fluids, when administered in-vivo and therefore provides prolonged release of tapentadol.

Another embodiment of the present invention provides an injectable composition comprising tapentadol or its pharmaceutically acceptable salt or ester, formulated as a liquid composition, and wherein the said composition forms an in-situ microparticles upon contact with body fluids, when administered in-vivo and thereby provides prolonged release of tapentadol.

Another embodiment of the present invention provides an injectable composition comprising tapentadol or its pharmaceutically acceptable salt or ester, formulated as a liquid composition, and wherein the said composition provides prolonged release of tapentadol.

Preferred embodiment of the present invention provides an injectable composition comprising tapentadol pamoate formulated as liquid composition wherein the said composition provides prolonged release of tapentadol.

Preferred embodiment of the present invention provides an injectable composition comprising tapentadol hemipamoate formulated as liquid composition wherein the said composition provides prolonged release of tapentadol.

Preferred embodiment of the present invention provides an injectable composition comprising engineered particles of tapentadol hemipamoate formulated as liquid composition wherein the said composition provides prolonged release of tapentadol.

Another preferred embodiment of the present invention provides an injectable composition comprising engineered particles of tapentadol hemipamoate formulated as lyophilized powder for reconstitution wherein the said composition provides prolonged release of tapentadol.

Another embodiment of the present invention provides an injectable composition comprising tapentadol or its pharmaceutically acceptable salt or ester, formulated as microparticles composition, and thereby provides prolonged release of tapentadol.

Another embodiment of the present invention provides an injectable composition comprising tapentadol or its pharmaceutically acceptable salt or ester and one or more biodegradable polymer, formulated as microparticles composition and thereby provides prolonged release of tapentadol.

Another embodiment of the present invention provides an injectable composition comprising tapentadol or its pharmaceutically acceptable salt or ester, formulated as solid implant composition, and thereby provides prolonged release of tapentadol.

Another embodiment of the present invention provides an injectable composition comprising tapentadol or its pharmaceutically acceptable salt or ester, formulated as liposome and thereby provides prolonged release of tapentadol.

Another embodiment of the present invention provides use of an injectable composition of tapentadol or its pharmaceutically acceptable salt or ester according to the present invention for treating pain.

The pain according to present invention is selected from but not limited to cancer pain, postoperative pain, diabetic nephropathy or pain associated with the medical conditions which include osteoarthritis, rheumatoid arthritis and the like.

Another embodiment of the present invention provides process for preparing an injectable composition comprising tapentadol or its pharmaceutically acceptable salt or ester, and wherein the said composition provides prolonged release of tapentadol.

Another embodiment of the present invention provides a process for preparing injectable composition comprising tapentadol or its pharmaceutically acceptable salt or ester through lyophilization process, and wherein the said composition provides prolonged release of tapentadol.

In another embodiment, the present invention provides an injectable composition comprising 1 to 75% w/w of tapentadol or its pharmaceutically acceptable salt or ester, preferably 5 to 70% w/w of tapentadol or its pharmaceutically acceptable salt or ester.

The injectable composition according to present invention administered to a subject, animals or humans, preferably via intramuscular, intraperitoneal, or subcutaneous route.

Injectable composition according to present invention is provided in vial or bottle as ready to use liquid formulation or as lyophilized powder or cake form for reconstitution.

Aqueous composition according to present invention is subjected to lyophilization techniques as known in the art to provide lyophilized powder or cake which can be reconstituted with suitable vehicle at the time of administration.

In-Situ Implant & In-Situ Microparticles Composition

Injectable composition of the present invention can be formulated as liquid composition, which forms an in-situ implant or in-situ microparticles upon contact with body fluids, when administered in-vivo. Liquid composition for in-situ implant according to present invention comprises one or more biodegradable polymer and solvent. Optionally the formulation may contain other pharmaceutically acceptable excipients to stabilize the formulation to attain a target release profile. Optionally, liquid composition for in-situ implant according to present invention is lyophilized, which can be reconstituted before administration.

When the liquid composition is injected into the IM/SC space through a needle, water in the tissue fluids causes the polymer to precipitate and trap the drug in the implant, which provides prolonged release of tapentadol.

For preparing in-situ microparticles drug is dissolved or dispersed in polymer solution. Polymer solution is prepared by dissolving biodegradable polymer in biocompatible solvent. Drug solution or dispersion obtained is then added to oil phase containing suitable stabilizer and subjected to homogenization to obtain an emulsion ready for injection. After injection of emulsion into the body solvent diffuses into body fluids, this leads to the polymer precipitation, and forms the microparticles in-situ. The duration and rate of release of tapentadol from the delivery system can be affected by type, molecular weight and concentration of polymer, oil phase concentration, hydrophilicity of the oil phase, size and shape of microparticles, type of biocompatible organic solvent.

Injectable Liquid Composition

Injectable composition of the present invention can be formulated as liquid composition of tapentadol for parenteral administration, which provides prolonged release. Tapentadol may be suspended and/or dispersed in the aqueous vehicle or in non-aqueous vehicle. The said composition further comprises one or more pharmaceutically acceptable excipients.

Injectable composition of tapentadol according to the present invention when formulated as liquid composition forms homogenous solution or forms aqueous/non-aqueous suspension/dispersion. Preferably, tapentadol forms aqueous suspension. Optionally, liquid composition according to present invention is lyophilized, which can be reconstituted before administration.

Liquid formulation according to present invention comprises tapentadol base or tapentadol monopamoate or hemipamoate. Preferably, liquid formulation comprises tapentadol hemipamoate. According to present invention the particle size (D90) of the suspended or dispersed particles in the liquid composition or particle size of lyophilized powder of tapentadol or its pharmaceutically acceptable salt or ester is less than 50 microns, preferably size of engineered particles is less than 30 microns, more preferably size of engineered particles is less than 15 microns, Most preferably size of engineered particles is less than 10 microns. Surprisingly it was observed that particle size of tapentadol or its pharmaceutically acceptable salt or ester, particularly tapentadol base and tapentadol hemipamoate interfere with the release of the drug, when formulated according to present invention. Therefore particle size optimization is very critical for desired release of the drug. Preferably, the particle size (D90) of the suspended or dispersed particles of tapentadol hemipamoate in the liquid composition is less than 50 microns, more preferably particle size is less than 15 microns. Also, the particle size (D90) of the suspended or dispersed particles of tapentadol hemipamoate in the liquid composition, after reconstitution of lyophilized powder with desired vehicle, is less than 50 microns, more preferably particle size is less than 15 microns pH of the liquid composition prepared according to present invention ranges from 3-9, preferably from 5-8.5.

Injectable aqueous suspension of Tapentadol can be used as a ready to use suspension or as lyophilized powder to improve the physical as well as chemical stability of the formulation.

Lyophilized powder can be prepared by the methods known in the art. Optionally, freeze drying protectants like cryoprotectants can be employed in the process of lyophilization. Cryoprotectants are the agents that protect the formulation composition from the deleterious effect of freezing. In case of injectable suspensions, cryoprotectants protects from agglomeration caused by the process of Lyophilization. Type and amount of cryoprotectant used in diluent of composition is critical for determining syrigibility as well as injectability of the composition after reconstitution of lyophilized formulation. Also, process and duration of freeze drying is critical to provide required cake or powder of liquid suspension.

Examples of cryoprotectants which can be used includes but not limited to, Mannitol, Lactose, Sucrose, Trehalose, Sorbitol, Glucose etc. A preferred cryoprotectant is Sucrose.

Microparticles Composition

Injectable composition of the present invention can be formulated as microparticle composition, prepared by double emulsion solvent evaporation method (W1/O/W2). The principal of encapsulation is based upon inducing phase separation of the polymer dissolved in an organic solvent (O phase) due to partial extraction of the solvent in a large volume of an external water phase (W2) and evaporation of the volatile solvent. The polymer then forms a coacervate enclosing the internal aqueous phase (W1) containing the active compound and microparticles are hardened under removal of residual solvent. The said composition may further comprises one or more pharmaceutically acceptable excipients.

Microparticles can also be prepared by coacervation method, single and double emulsion—solvent evaporation, spray drying method, lyophilization or freeze drying and supercritical fluid technology. Microparticles prepared according to present invention are dispersed or suspended in suitable vehicle for injectable delivery.

The size of the microparticles (D90) prepared according to present invention is less than 200 microns more preferably size is less than 150 microns, most preferably size is less than 100 micron.

pH of the microparticles composition prepared according to present invention ranges from 3-8, preferably from 5-8.

Liposome/Non Ionic Surfactant Based Composition

Injectable composition of the present invention can be formulated as lipid/non ionic surfactant based vesicles which provide prolonged release including liposome or niosome. Preferable lipid/non ionic surfactant based vesicles are liposomes. Liposomal composition may further comprises one or more pharmaceutically acceptable excipients.

Present invention further provides a process for the preparation of long acting pharmaceutical composition of tapentadol or it pharmaceutically acceptable salts or esters, which is formulated as lipid/non ionic surfactant based vesicles, comprises:
 a) dissolve lipids/non ionic surfactant in suitable organic solvent or combination thereof;
 b) separately dissolve tapentadol or its pharmaceutically acceptable salts or esters in suitable aqueous buffer or add to step a); and
 c) Prepare lipid/non ionic surfactant based vesicles by any suitable method known in the art.

pH of the composition comprising lipid/non ionic surfactant based vesicles prepared according to present invention ranges from 3-8, preferably from 5-8.

Solid Implant Composition

Injectable composition of the present invention can be formulated as solid implant. Briefly, the drug and one or more pharmaceutically acceptable excipients are combined and fed to a melt extruder to produce a bulk rod, which is then cut to produce the unit dose. The excipients are selected from but not limited to biodegradable polymers, solid lipids and plasticizers.

In some embodiments of the present invention, biodegradable polymer is used. Suitable biodegradable polymers can be used as known in art, including but not limited to a group comprising lactic acid-based polymers such as polylactides for example poly (D,L-lactide) or PLA; glycolic acid-based polymers such as polyglycolides (PGA); poly (D,L-lactide-co-glycolide) which is PLGA; polyvinylpyrrolidone; polystyrene; synthetic celluloses; polyacrylic acids; polybutyric acid; triblock copolymers (PLGA-PEG-PLGA), triblock copolymers (PLA-PEG-PLA), triblock copolymers (PEG-PLGA-PEG), multiblock copolymer, poly (ethylene oxide)-poly (propylene oxide)-poly (ethylene oxide) tri-block copolymers (PEO-PPO-PEO), polyethylene glycol; or mixtures thereof.

In some embodiments of the present invention biocompatible organic solvent is used, which is defined here as the organic solvent generally does not react or cause any untoward interaction with the biological tissues. Biocompatible solvent is selected from a group comprising triacetin, ethanol, benzyl alcohol, 1-butanol, 2-butanol, chloroform, acetic acid, isopropyl alcohol, acetonitrile, N-methyl-2-pyrrolidone (NMP), 2-pyrrolidone, miglyol, glycerol, methyl acetate, methyl isobutyl ketone, benzyl benzoate, propylene glycol, dimethyl isosorbide, propylene carbonate, ethyl acetate, ethyl lactate, dimethyl sulfone, N,N-diethyl-m-toluamide, methyl ethyl ketone, dimethylformamide, dichloromethane, benzonitrile, dimethyl isosorbide, dimethyl sulfoxide, dimethyl acetamide, tetrahydrofuran, caprolactam, decymethylsulfoxide, oleic acid, and I-dodecylazacycloheptan-2-one or mixtures thereof.

In some embodiments of the present invention, the composition contains a suitable aqueous vehicle which is water for injection (WFI) and which optionally comprises a suspending agent or viscosity modifying agent and wetting agent and optionally one or more of a preservative, pH adjusting agent, buffer, isotonizing agent or osmolity maintaining agent and release rate retarding agent.

In some embodiments of the present invention, the composition contains non-aqueous vehicles including but not limited to cottonseed oil, dibutyl phthalate, diethyl phthalate, dimethyl ether, dimethyl phthalate, dimethyl sulfoxide, dimethylacetamide, ethyl acetate, ethyl lactate, ethyl oleate, glycerin, glycofurol, isopropyl alcohol, isopropyl myristate, isopropyl palmitate, light mineral oil, medium-chain triglycerides (MCTs), methyl lactate, mineral oil, monoethanolamine, octyldodecanol, olive oil, peanut oil, polyethylene glycol, castor oil, propylene carbonate, propylene glycol, pyrrolidone, safflower oil, sesame oil, soybean oil, sunflower oil, triacetin, tricaprylin, triethanolamine, triethyl citrate, triolein, alcohol, almond oil, benzyl alcohol, benzyl benzoate, butylene glycol, carbon dioxide or mixtures thereof. Optionally, a pharmaceutically acceptable excipient, such as thickening agent, preservatives, antioxidants, and any combination thereof, can be added to the non-aqueous vehicle.

In some embodiments of the present invention thickening agent is used, including but not limited to aluminum monostearate, ethyl cellulose, triglycerides, hydrogenated castor oil and the like or mixture thereof.

The injectable composition according to present invention further comprises one or more pharmaceutically acceptable ingredients selected from but not limited to buffering agent, wetting agent, viscosity modifying agent, release rate retarding agent, isotonicity agent, preservative, stabilizer, pH adjusting agent, plasticizers and the like or mixtures thereof.

In some embodiments of the present invention wetting agent is used, including but not limited to benzalkonium chloride, benzethonium chloride, cetylpyridinium chloride, docusate sodium, glycine, phospholipids, polaxomers, polyoxyethylene alkyl ethers such as polyoxyethylene monolauryl ether, alkylphenylpolyoxy-ethylene ethers (Triton-X), polyoxyethylene-polyoxypropylene copolymer (Poloxamer, Pluronic), polyoxyethylene castor oil derivatives, polyoxyethylene sorbitan fatty acid esters, polyoxyethylene stearates, sodium lauryl sulfate, sorbitan esters, tricaprylin and the like or mixtures thereof.

In some embodiments of the present invention release rate retarding agent is used, including but not limited to modified dextrans, sucrose acetate isobutyrate (SAIB), medium chain triglycerides, glucose, polymeric solutions (prepared by mixing polymers in suitable solvent) and the like or mixtures thereof.

In some embodiments of the present invention stabilizers is used, including but not limited to mannitol, sorbitol, sucrose, glycine, lactose, amino acids, sugars, alpha-tocopherol, ascorbic acid, butylated hydroxyanisole, butylated hydroxytoluene, citric acid, fumaric acid, malic acid, monothioglycerol, propionic acid, propyl gallate, sodium ascorbate, sodium bisulfite, sodium metabisulfite, potassium metabisulfite, sodium sulfite, tartaric acid, vitamin E and the like or mixtures thereof.

In some embodiments of the present invention pH adjusting agent is used, including but not limited to sodium hydroxide, hydrochloric acid and the like or mixtures thereof.

In some embodiments of the present invention plasticizers is used, including but not limited to polyethylene glycol, stearic acid, palmitic acid, cholesterol, cetyl palmitate, poloxamer and the like or mixtures thereof.

Preservative for use in the present invention is chosen in quantities that preserve the composition. Suitable preservatives used in some of the embodiments of present invention include, but are not limited to, benzalkonium chloride, methyl, ethyl, propyl or butylparaben, benzyl alcohol, phenylethyl alcohol, benzethonium, chlorobutanol, potassium sorbate or combination thereof.

In some embodiments of the present invention buffering agent is used, including, but not limited to, salts of citrate, acetate, or phosphate or mixtures thereof.

In some embodiments of the present invention isotonicity agent is used, including, but not limited to sodium chloride (NaCl), potassium chloride, sugars and sugar alcohols including but not limited to glucose, sucrose, trehalose or glycerol and any component from the group of amino acids, sugars, salts alone or in combinations.

Viscosity modifying agent for used according to the invention are known to a skilled person from available art, including but not limited to acacia, agar, alginic acid, bentonite, carboxymethylcellulose calcium, carboxymethylcellulose sodium, carrageenan, colloidal silicon dioxide, ethyl cellulose, hydrogenated vegetable oil, hydroxyethyl cellulose, hydroxyethylmethyl cellulose, hydroxypropyl cellulose, hydroxypropyl starch, hypromellose, methylcellulose, myristyl polyethylene glycol, polyvinyl acetate phthalate, polyvinyl alcohol, potassium chloride, povidone starch, stearyl alcohol, sucrose, or mixture thereof.

Lipid used according to present invention is of synthetic or semi-synthetic origin. Examples of lipids are known to a skilled person from available are, including but not limited to phosphatidylcholines, dimyristoylphosphatidylcholine (DMPC), Dipalmitoylphosphatidylcholine (DPPC), Disteroylphosphatidylcholine (DSPC), phosphatidylglycerol, cholesterol and the like or mixture thereof. In some embodiments of the present invention, the composition contains solid lipids which include tri-stearin, trimyristin, tripalmitin, Glyceryl dibehenate, Dodecanoic acid, 1,1',1"-(1,2,3-propanetriyl) ester, cholesterol, stearic acid, palmitic acid and the like or mixtures thereof.

In some embodiments of the present invention non ionic surfactants is used, including but not limited to acetyl alcohol, cocamide diethanolamine, cocamide monoethanolamine, poloxamer, polyglycerol, polysorbate, spans, tween and mixture thereof.

The invention will be further illustrated by the following examples, however, without restricting its scope to these embodiments.

EXAMPLES

Example 1

Dispersion of Engineered Particles of Tapentadol in Non-Aqueous Vehicle 5-70% of Tapentadol of engineered particle size is dispersed in 60-95% of cotton seed oil.

Example 2

Dispersion of Engineered Particles of Tapentadol in Aqueous Vehicle

4% Mannitol, 5% sodium caboxymethyl cellulose, 0.1% Tween 80 and water for injection (q.s) are mixed to form aqueous vehicle.

5-70% of Tapentadol pamoate (engineered particle size) is dispersed in 60-95% of aqueous vehicle.

Example 3

In-Situ Microparticles 1. 5-50% of PLGA is dissolved in 10-50% of N-methyl pyrrolidone
2. 5-70% of Tapentadol is dissolved in same solvent used in step 1.
3. Solution of step 2 is homogenized in Miglyol 812 (Caprylic triglyceride, an oily vehicle) containing Span 80(Sorbitan Laurate).

Example 4, 5 and 6

In Situ Implants of Tapentadol

| Sr No | Ingredients | Example 4 | Example 5 | Example 6 |
|---|---|---|---|---|
| 1 | Tapentadol | 5-70% | 5-70% | 5-70% |
| 2 | PLGA | 10-60% | 10-60% | — |
| 3 | Benzyl benzoate | — | 0.5-30% | — |
| 4 | NMP | 20-90% | 20-90% | 20-90% |
| 5 | PLGA-PEG-PLGA | — | — | 10-60% |

1. Dissolve polymer PLGA (example 4 and 5) or PLGA-PEG-PLGA (example 6) in solvent N-methyl pyrrolidone (Example 4, 5 and 6) and benzyl benzoate (Example 5).
2. Dissolve Tapentadol in solution of step 1.

Example 7

Solid Implant of Tapentadol

1. Mix 5-70% Tapentadol with 10-95% PLGA.
2. Extrude the mixture of step 1 at 70-80° C.
3. Cut extrudes in appropriate size.

Example 8

Microparticles of Tapentadol Using Spray Drying Technique

1. Dissolve 10-90% PLGA in ethyl acetate (q.s.).
2. Disperse 5-70% Tapentadol in solution as prepared in step 1.
3. Spray dry step 2 dispersion.

Example 9

Microparticles of Tapentadol Using Spray Drying Method

1. Dissolve 10-90% PLGA in acetone (q.s).
2. Dissolve 5-70% Tapentadol in methanol (q.s).
3. Add the solution of step 2 to solution of step 1.
4. Spray dry the solution of step 3 through fluid nozzle.

Example 10

Microparticles of Tapentadol Using Double Emulsion Method

1. Dissolve 10-90% PLGA in ethyl acetate (q.s.).
2. Dissolve 5-70% tapentadol in WFI (q.s.).

3. Mix contents of step 1 and step 2 using homogenizer to form primary emulsion.
4. Add primary emulsion to PVA solution (q.s.) using homogenizer or overhead stirrer to form secondary emulsion.
5. Remove ethyl acetate under vacuum or by washing to solidify the microparticles.
6. Lyophilize the microparticles

Example 11

Liposome of Tapentadol

1. Dissolve 10-90% of DSPC and 5-50% of Cholesterol in mixture of Chloroform (q.s.) and methanol (q.s.).
2. Prepare dry thin film of step 1 solution using Rotavapour
3. Hydrate step 2 lipid film using 5-70% of tapentadol solution to get liposome.
4. Lyophilize the liposomal suspension.

Example 12, 13 and 14

Non-Aqueous Composition

| Sr No | Ingredients | Example 12 | Example 13 | Example 14 |
|---|---|---|---|---|
| 1. | Tapentadol | 12% | 12% | 12% |
| 2. | MCT oil | q.s. to 100% | q.s. to 100% | — |
| 3. | Sesame oil | — | — | . . . q.s. to 100% |
|  | Homogenization with high speed homogenizer | 10 min 15000 rpm followed by 5 min 20000 rpm | dispersing at 10000 rpm for 2 min | 10 min 15000 rpm followed by 5 min 20000 rpm |
|  | D90 | 94.14 micrometer | 28.74 micrometer | 89.58 micrometer |

Tapentadol base was added in oily vehicle under stirring to form a homogenous paste followed by addition of remaining vehicle to make up the volume. Solution was homogenized with high speed homogenizer.

Example 15

Aqueous Suspension

| Sr No | Ingredients | Quantity |
|---|---|---|
| 1 | Tapentadol Base | 12% |
| 2 | Aqueous vehicle | q.s. to 100% |

Composition of Aqueous Vehicle

| Sr No | Ingredients | Quantity |
|---|---|---|
| 1 | Na CMC | 0.9% |
| 2 | Tween 80 | 0.1% |
| 3 | Mannitol | 4.5% |
| 4 | WFI | q.s. to 100% |

Tapentadol base was added in aqueous vehicle under stirring to form a homogenous paste followed by addition of remaining vehicle to make up the volume. Solution was homogenized with high speed homogenizer. pH of the solution was adjusted by adding glacial acetic acid.

Example 16

In-Situ Implant

| Sr No | Ingredients | Quantities |
|---|---|---|
| 1. | Tapentadol | 17.39% |
| 2. | PLGA | 37.17% |
| 3. | NMP | 45.43% |

PLGA was dissolved in NMP. Obtained polymeric solution was added into the tapentadol base and mixed to dissolve tapentadol. The solution was filled into the vials.

Example 17, 18 19, 20

Aqueous Suspension

| Sr No | Ingredient | Example 17 | Example 18 | Example 19 | Example 20 |
|---|---|---|---|---|---|
|  |  | Composition | | | |
| 1. | Tapentadol hemipamoate | 11.28% | 11.28% | 11.28% | 11.28% |
| 2. | Diluent | q.s. to 100% | q.s to 100% | q.s to 100% | q.s to 100% |
|  | Diluent composition | Na CMC . . . 9 mg Tween 80 . . . 1 mg Mannitol . . . 45 mg W.F.I. (q.s.) . . . 1 ml | Na CMC . . . 9 mg Tween 80 . . . 1 mg Mannitol . . . 45 mg W.F.I. (q.s.) . . . 1 ml | Na CMC . . . 9 mg Tween 80 . . . 1 mg Mannitol . . . 45 mg W.F.I. (q.s.) . . . 1 ml | Povidone K12 . . . 5 mg Tween 80 . . . 1 mg Mannitol . . . 45 mg Sodium dihydrogen phosphate dihydrate . . . 6 mg WFI - q.s to 1 ml |
|  | Processing Parameters | 10 min High speed homogenization at 10000 RPM followed by 3 min at 10000 RPM | 10 min High speed homogenization at 10000 RPM followed by 10 min at 15000 RPM | 10 min High speed homogenization at 15000 RPM followed by 10 min at 17000 RPM followed by 5 min at 20000 RPM followed by 5 min at 20000 RPM | 20 min High speed homogenization at 15000 RPM followed by 20 min High pressure homogenization at 16000 PSI |
|  | D90 | 28.84μ | 16.59μ | 8.31μ | 2.09μ |

Procedure: (Example 17-18-19)

Sodium CMC was added in WFI under stirring and allowed to dissolve. While stirring Tween 80 and Mannitol was added and dissolved. Tapentadol hemipamoate was then dispersed in stirred mixture which was then homogenized using high speed homogenizer to achieve the desired particle size distribution and finally filled into sterile container.

Procedure (Example 20)

Povidone K12 was added in WFI under stirring and allowed to dissolve. While stirring Sodium dihydrogen phosphate dihydrate, Tween 80 and Mannitol was added and dissolved. Tapentadol hemipamoate was then dispersed in stirred mixture which was then homogenized using high speed homogenizer to achieve the uniform dispersion and dispersion was passed through high pressure homogenizer to achieve the desired particle size distribution and finally filled into sterile container.

It was observed that composition of diluent was very important to achieve desired injectability and syringeability.

Example 21

Microparticle

| Sr No | Ingredients | Quantities |
| --- | --- | --- |
| 1. | Tapentadol base | 31.3% |
| 2. | PLGA | 68.6% |

Organic phase was prepared by dissolving PLGA (50:50 DLG 2A-1.75 g) in ethyl acetate (3.25 g) to obtain 35% w/w polymer solution. Tapentadol base (0.8 g) was then dissolved in polymer solution. The aqueous phase consisted of 25 ml 1% PVA in WFI containing 6% ethyl acetate. Organic phase was added to precooled aqueous phase (5±3° C.) under stirring and both phases were emulsified using high speed homogenization for 3 min at 3600 rpm to get o/w emulsion. The resulting 0/W emulsion was immediately poured into 250 ml of 1% PVA solution for hardening of microparticles. The microparticles were collected by vacuum filtration. Collected microparticles were suspended in 4.5% mannitol solution and filled in vials and freeze dried. Freeze dried composition was reconstituted with aqueous diluent containing 0.1% Tween 80 and 0.9% sodium CMC.

Example 22, 23

Aqueous Suspension Lyophilization

| Sr No | Ingredient | Example 22 | Example 23 |
| --- | --- | --- | --- |
| | | Composition | |
| 1. | Tapentadol hemipamoate | 18.0% w/w | 19.3% w/w |
| 2. Diluent composition | Diluent | q.s to 100% w/w Mannitol . . . 8.78% w/w Povidone K12 . . . 0.46% w/w Tween 80 . . . 0.05% w/w WFI . . . q.s. to 100% | q.s to 100% w/w Sucrose . . . 8.60% w/w Povidone K12 . . . 0.46% w/w Tween 80 . . . 0.05% w/w WFI . . . q.s. to 100% |

Procedure:

Tapentadol hemipamoate was dispersed in the diluent and then homogenized using high speed homogenizer (15 min at 15000 rpm) to achieve the uniform dispersion and dispersion was passed through high pressure homogenizer (2 min at 10000 PSI followed by 5 min at 15000 PSI followed by 10 min at 20000 PSI) for particle size reduction. 3.2 ml of the suspension was lyophilized in 5 ml vials and reconstituted with initial volume of water. It was observed that formulation containing sucrose as a cryoprotectant was easy to reconstitute compared to formulation containing Mannitol as a cryoprotectant.

Lyophilization Cycle:

| Sr. No. | Stages | | Pressure (mtorr) | Duration (Hr:min) |
| --- | --- | --- | --- | --- |
| | | Temperature (° C.) | | |
| 1 | Freezing | | | |
| | 1 (Freezing) | −40 | | 2:00 |
| | 2 (Freezing) | −20 | | 1:30 |
| | 3 (Freezing) | −40 | | 2:00 |
| | (Condenser Temp) | −40 | | |
| | Vacuum required | | 200 | |
| | Vacuum stabilization time | | | 0:01 |
| | | Shelf Temp. (° C.) | | |
| 2 | Primary Drying | | | |
| | Step 1 | −30 | 200 | 5:00 |
| | Step 2 | −20 | 200 | 5:00 |
| | Step 3 | −10 | 150 | 6:00 |
| | Step 4 | 0 | 150 | 5:00 |
| | Step 5 | 10 | 100 | 5:00 |
| 3 | Secondary Drying | 25 | 50 | 10:00 |
| | Total Cycle time | | | 41:30:00 |

Example 24

Aqueous Suspension Lyophilization

| Sr No | Ingredients | Example 24 |
| --- | --- | --- |
| | | Composition |
| 1. | Tapentadol hemipamoate | 20.0% w/w |
| 2. Diluent composition | Diluent | q.s to 100% w/w Sucrose . . . 7.50% w/w Povidone K12 . . . 0.50% w/w Tween 80 . . . 0.05% w/w WFI . . . q.s. to 100% |

Procedure:

Tapentadol hemipamoate was dispersed in the diluent and then homogenized using high speed homogenizer (15 min at 15000 rpm) to achieve the uniform dispersion and dispersion was passed through high pressure homogenizer 15 min at 5000 PSI followed by 15 min at 10000 PSI followed by 10 min at 15000 PSI) for particle size reduction. 3 ml of the suspension was lyophilized in 5 ml vials and reconstituted with initial volume of water. Cake obtained was intact and reconstituted with initial volume of water.

Lyophilization Cycle:

| Stages | Temp. (° C.) | Pressure (mtorr) | Rate (° C./min)/Hold | Duration (Hr:min) |
|---|---|---|---|---|
| Freezing | | | | |
| Step 1 | 5 | | 1 | 0:20 |
| Step 2 | 5 | | Hold | 0:30 |
| Step 3 | −5 | | 1 | 0:10 |
| Step 4 | −5 | | Hold | 0:30 |
| Step 5 | −40 | | 1 | 0:35 |
| Step 6 | −40 | | Hold | 1:00 |
| Final set Point | −40 | | | |
| Extra freezing time | | | | 0:00 |
| Vacuum required | | 57 | | |
| Primary Drying | | | | |
| Step 1 | −37 | 57 | 0.5 | 0:06 |
| Step 2 | −37 | 57 | Hold | 3:47 |
| Step 3 | −26.6 | 57 | 0.5 | 0:21 |
| Step 4 | −26.6 | 57 | Hold | 3:06 |
| Step 5 | −23.7 | 57 | 0.5 | 0:06 |
| Step 6 | −23.7 | 57 | Hold | 21:30 |
| Secondary Drying | | | | |
| Step 1 | 40 | 57 | 0.1 | 10:37 |
| Step 2 | 40 | 57 | Hold | 4:00 |
| Total Cycle Time: | | | | 46 hr:38 min |

Example 25 and 26

Aqueous Suspension Lyophilization

| Sr No | Ingredient | Example 25 | Example 26 |
|---|---|---|---|
| 1. | Tapentadol hemipamoate | 19% w/w | 19% w/w |
| 2. | Diluent | q.s. to 100% | q.s to 100% |
| Diluent composition | | Povidone K12 . . . 5 mg Tween 80 . . . 1 mg Sucrose . . . 75 mg WFI - q.s to 1 g | |
| Processing Parameters | | 20 min High speed homogenization at 15000 RPM followed by High pressure homogenization at 5000 PSI for 15 min, 10000 PSI for 15 min and 15000 PSI for 10 min | 3 min High speed homogenization at 4000 RPM followed by 5 min at 10000 RPM and 3 min at 15000 RPM. |
| D(90) | | 2.599 | 30.507 |

Povidone K12 was added in WFI under stirring and allowed to dissolve. While stirring Tween 80 and Mannitol was added and dissolved. Tapentadol hemipamoate was then dispersed in stirred mixture which was then homogenized to achieve the desired particle size distribution. Final suspension was filled in 5 ml glass vial and lyophilized by using the process according to Example 24. Obtained cake was reconstituted with mixture of $NaH_2PO_4.2H_2O$ and water.

In-Vivo Characterization in Wistar Rats:

A) Composition of Example 17, 18, 19, 20 and 21

Formulations of Example 17-21 were administered to male wistar rats. Each group (N=5) was administered a single dose of formulation intramuscularly containing 6 mg equivalent tapentadol base. Blood samples were withdrawn at predefined time interval for measurement of tapentadol. Results are illustrated in FIG. 1.

In-Vivo Characterization in Beagle Dogs:

Formulation prepared according to Example 25 and 26 were administered to male Beagle Dogs. Each group (N=3) was administered a single dose of formulation (eq to 12 mg/kg Tapentadol base) intramuscularly. Blood samples were withdrawn at predefined time interval for measurement of tapentadol. Results are illustrated in FIG. 2.

The invention claimed is:

1. An injectable composition comprising tapentadol hemipamoate, wherein the said composition provides prolonged release of tapentadol for at least 24 hours.

2. The injectable composition according to claim 1, wherein composition is formulated as solid implant, in-situ implant, microparticle, in-situ microparticle, liposomal or liquid composition.

3. The injectable composition according to claim 2, wherein composition is formulated as liquid composition.

4. The injectable composition according to claim 3, wherein the composition comprises engineered particles of tapentadol hemipamoate.

5. The injectable composition according to claim 4, wherein the particle size (D90) of the tapentadol hemipamoate is less than 50 microns.

6. An injectable composition comprising engineered particles of tapentadol hemipamoate, wherein the particle size (D90) of the tapentadol hemipamoate is less than 50 microns and said composition provides prolonged release of tapentadol.

7. The injectable composition according to claim 6, wherein composition is formulated as liquid composition or lyophilized powder for reconstitution.

8. The injectable composition according to claim 1, wherein release of the tapentadol is up to one month.

9. The injectable composition according to claim 4, wherein the particle size (D90) of the tapentadol hemipamoate is less than 30 microns and said composition provides prolonged release of tapentadol.

10. The injectable composition according to claim 4, wherein the particle size (D90) of the tapentadol hemipamoate is less than 15 microns and said composition provides prolonged release of tapentadol.

11. The injectable composition according to claim 4, wherein the particle size (D90) of the tapentadol hemipamoate is less than 10 microns and said composition provides prolonged release of tapentadol.

12. The injectable composition according to claim 6, wherein the particle size (D90) of the tapentadol hemipamoate is less than 30 microns and said composition provides prolonged release of tapentadol.

13. The injectable composition according to claim 6, wherein the particle size (D90) of the tapentadol hemipamoate is less than 15 microns and said composition provides prolonged release of tapentadol.

14. The injectable composition according to claim 6, wherein the particle size (D90) of the tapentadol hemipamoate is less than 10 microns and said composition provides prolonged release of tapentadol.

15. The injectable composition according to claim 1, wherein release of tapentadol is up to 7 days.

16. The injectable composition according to claim 1, wherein release of the tapentadol is up to 5 days.

* * * * *

UNITED STATES PATENT AND TRADEMARK OFFICE
CERTIFICATE OF CORRECTION

PATENT NO. : 9,629,818 B2  
APPLICATION NO. : 14/439840  
DATED : April 25, 2017  
INVENTOR(S) : Nadkarni et al.

Page 1 of 1

It is certified that error appears in the above-identified patent and that said Letters Patent is hereby corrected as shown below:

In the Specification

In Column 1 at Line 9, change "PCT/IB2012/058082" to -- PCT/IB2012/056082 --

Signed and Sealed this  
Third Day of October, 2017

Joseph Matal  
*Performing the Functions and Duties of the*  
*Under Secretary of Commerce for Intellectual Property and*  
*Director of the United States Patent and Trademark Office*